United States Patent
Bernacca et al.

(10) Patent No.: US 6,251,142 B1
(45) Date of Patent: Jun. 26, 2001

(54) IMPLANTATION DEVICE AND A KIT INCLUDING THE DEVICE

(75) Inventors: Giuliana Bernacca, Marina di Massa; Maria Curcio, Saluggia; Leopoldo Della Ciana, Lugo; Anilla Massaglia, Turin, all of (IT)

(73) Assignee: Sorin Biomedica Cardio S.p.A. (IT)

( * ) Notice: Subject to any disclaimer, the term of this patent is extended or adjusted under 35 U.S.C. 154(b) by 0 days.

(21) Appl. No.: 08/987,365

(22) Filed: Dec. 9, 1997

(30) Foreign Application Priority Data

Dec. 10, 1996 (IT) .................................. T096A1002

(51) Int. Cl.⁷ ....................................... A61F 2/06
(52) U.S. Cl. .................. 623/23.57; 623/23.7; 623/1.46; 427/2.25; 427/2.24
(58) Field of Search ................. 623/1, 12, 1.42, 623/1.43, 1.46, 1.48, 1.47, 23.57; 435/181; 427/2.1–2.31, 2.34

(56) References Cited

U.S. PATENT DOCUMENTS

| | | | | |
|---|---|---|---|---|
| 4,451,568 | * | 5/1984 | Schneider et al. | 435/181 |
| 4,478,914 | | 10/1984 | Giese . | |
| 4,795,459 | | 1/1989 | Jauregui . | |
| 5,092,885 | * | 3/1992 | Yamada et al. | 623/11 |
| 5,578,073 | * | 11/1996 | Haimovich et al. | 623/1 |
| 5,700,286 | * | 12/1997 | Tartaglia et al. | 623/1 |
| 5,811,447 | * | 9/1998 | Kunz et al. | 514/411 |
| 5,830,879 | * | 11/1998 | Isner | 514/44 |
| 5,833,651 | * | 11/1998 | Donovan et al. | 604/53 |
| 5,840,009 | | 11/1998 | Fischell et al. . | |
| 5,843,156 | * | 12/1998 | Stepian et al. | 623/1 |
| 5,851,231 | * | 12/1998 | Wolff et al. | 623/1 |
| 5,925,353 | * | 7/1999 | Mosseri | 424/178.1 |
| 5,925,552 | * | 7/1999 | Keogh et al. | 435/174 |
| 6,001,350 | * | 12/1999 | Mulligan et al. | 424/93.21 |
| 6,045,788 | * | 4/2000 | Smith | 424/85.2 |

FOREIGN PATENT DOCUMENTS

| | | |
|---|---|---|
| 0 496 074 A1 | 12/1991 | (EP) . |
| WO 90/00343 | 1/1990 | (WO) . |
| WO 90/01305 | 2/1990 | (WO) . |
| WO 96/09309 | 3/1996 | (WO) . |
| WO 96/38726 | 12/1996 | (WO) . |
| WO 98/43694 | 10/1998 | (WO) . |
| WO 99/09912 | 3/1999 | (WO) . |

OTHER PUBLICATIONS

European Search Report on European Patent Application No. EP 97 12 1538, including Annex, dated Jul. 7, 2000, 3 pages.

* cited by examiner

Primary Examiner—David H. Willse
Assistant Examiner—Suzette J. Jackson
(74) Attorney, Agent, or Firm—Popovich & Wiles, P.A.

(57) ABSTRACT

The apparatus comprises an implantation device having a body, the surface of which has at least a portion coated with a receptor, and a preparation containing a ligand formed from the combination of an active principle with a substance capable of binding to the receptor. This preparation may be brought into contact when desired with the implantation device which is, for example, a stent.

18 Claims, No Drawings

IMPLANTATION DEVICE AND A KIT INCLUDING THE DEVICE

FIELD OF THE INVENTION

The present invention concerns an implantation device, a method for its manufacture and a kit including it.

The invention has been developed with particular attention to its possible application to so-called stents for angioplasty. The invention is, however, applicable to implantation devices generally and should not therefore be understood as limited to the specific field of use referred to below in the present description.

BACKGROUND OF THE INVENTION

The term "stent for angioplasty" is intended generally to indicate devices intended for endoluminal application (for example, in a blood vessel, in association with percutaneous transluminal coronary angioplasty, or PTCA), usually effected by means of catheterisation of a stenotic site dilated using PTCA or ablation. The in situ expansion of the stent stabilises the expanded lumen with a consequent reduction in the likelihood of restenosis, the likelihood of which is very high (approximately 40%) in the case of PTCA alone.

The local support of the lumen by the stent, which is left in its expanded state at the treated site, avoids the restenosis of the site. The use of substantially similar structures to achieve the in situ expansion and anchorage of vascular grafts has already been proposed in the art: naturally, this possible extension of the field of application is also to be understood as coming within the ambit of the invention.

For a general review of vascular stents, reference may usefully be made to the work "Textbook of Interventional Cardiology" edited by Eric J. Topol, W.B. Saunders Company, 1994 and, in particular, to section IV of volume II, entitled "Coronary Stenting".

Many patent documents have also addressed this problem, for example, U.S. Pat. No. 4,776,337, U.S. Pat. No. 4,800,882, U.S. Pat. No. 4,907,336, U.S. Pat. No. 4,886,062, U.S. Pat. No. 4,830,003, U.S. Pat. No. 4,856,516, U.S. Pat. No. 4,768,507, and U.S. Pat. No. 4,503,569.

However, the implantation of these devices may give rise to secondary pathological phenomena such as, for example, acute thrombosis which requires additional antithrombogenic treatment that is usually administered systemically, or an excessive thickening of the neointima (hyperplasia), or spasms of the vascular wall.

Various solutions have been proposed in the past in order to overcome these negative effects.

One line of research generally envisages overcoming the aforesaid negative phenomena by way of radioactive treatments. This first line of investigation is documented, for example, in the following works:

"Intracoronary Radiation Before Stent Implantation Inhibits Neointima Formation in Stented Porcine Coronary Arteries" by Ron Waksman et al., Circulation, 1995; 92; 1383–1386;

"Radioactive Stents for the Prevention of Neointimal Hyperplasia" by Tim A. Fischell, from "The new manual of interventional cardiology", Physician's Press, Birmingham, chapter 18 (1996), p. 134 ss;

"Pure β-Particle-Emitting Stents Inhibit Neointima Formation in Rabbits", by Cristoph Hehrlein et al., Circulation 1996; 93; 641–645;

"Inhibition of Neointimal Proliferation With Low-Dose Irradiation From a β-Paticle-Emitting Stent" by John R. Laird et al., Circulation; 1996; 93; 529–536; and "The Beta-Particle-Emitting Radioisotope Stent (Isostent): Animal Studies and Planned Clinical Trials" by Tim A. Fischell et al., Am. J. Cardiol. 1996; 78 (suppl. 3A); 45–50.

Irrespective of its ultimate effectiveness, this solution encounters an essentially practical difficulty caused by the fact that, in most cases, the use of such a stent assumes the typical features of radiotherapy and/or nuclear medicine. This means that it is necessary to operate in a specifically equipped and authorised environment: this factor has the effect of negating many of the intrinsic advantages of the stent such as, in the first instance, the introduction of techniques once limited to the area of cardiac surgery into much simpler methods of intervention (catheterisation) which can practically be effected at the out-patient level.

Another line of research concerns substantially the administration and/or the localised release of active substances in the zone of the stent. This latter line of research is documented, for example, in the following works:

"Local Drug Delivery: The Development of a Drug Delivery Stenf" by Richard Stack, The Journal of Invasive Cardiology, Vol. 8, No. 8, October 1996 pages 396–397;

"Local Intraluminal Infusion of Biodegradable Polymeric Nanoparticles" by Louis A. Guzman et al., Circulation, 1996; 94; 1441–1448;

"Local Angiopeptin Delivery Using Coated Stents Reduces Neointimal Proliferation in Overstretched Porcine Coronary Arteries" by Ivan De Schreerder et al., J. Invas. Cardiol. 1996; 8; 215–222.

Many applicational problems are caused by this mode of operation, mainly linked to the specific solutions adopted which are, in any case, related to the fact that it enables little, and maybe even no, flexibility in terms of the timing of the association with the stent of the active substance and/or the possible variation of this latter. In addition, the problem exists of preventing the agent or agents intended for administration in the zone of the stent being delivered or transported to different areas where they could have negative or damaging effects. Other difficulties may arise, for example, in ensuring the permanence and the gradual release over time of active substances capable of being, as it were, washed away by the blood passing through the stent (or the implantation device in general). There are also cases in which it is desirable to be able to supply the site of the implantation device at successive intervals with active substances which, clearly, cannot be applied simultaneously to the device before implantation due to restrictions in their bonding chemistry.

For completeness, reference may also be made to biodegradable stents as illustrated, for example, in the work "Biodegradable Stents: The Future of Interventional Cardiology?" by M. Labinaz et al., Journal of International Cardiology, Vol. 8, No. 4, 1995, pp. 395–405. The main disadvantage of this solution clearly resides in the fact that, at least in the long term when the stent has completely or substantially degraded, it becomes less able mechanically to support the vessel wall against the risk of collapse.

SUMMARY OF THE INVENTION

The object of the present invention is thus to provide an implantation device which allows various kinds of active principle to be administered to the patient in whom the implantation has been made, which is very versatile both in terms of the principle to be applied and the timing of its association with the implantation device, and which avoids the disadvantages of the known solutions described above.

This object is achieved by virtue of an implantation device characterised in that at least a portion of the surface of the body of said device is coated with a receptor capable of binding selectively with a ligand formed by combining an active principle with a substance capable of binding specifically to the receptor.

A kit comprising a coated implantation device of the type described above and a preparation containing the ligand, which preparation is capable of being brought in contact with the device, as required, comprises a further subject of the invention.

In one aspect, this invention is an implantation device, such as a stent, comprising a body having a surface, wherein at least a portion of the surface is coated with a receptor capable if binding with a ligand formed by combining an active principle with a substance capable of binding to the receptor.

In a preferred embodiment, the receptor is avidin, streptavidin, biotin, antigens, antibodies, lectin or glycoprotein.

In another preferred embodiment, the receptor and the substance in the ligand capable of binding with the receptor is streptavidin-biotin, biotin-streptavidin, avidin-biotin, biotin-avidin, antigen-antibody, antibody-antigen, lectin-glycoprotein or glycoprotein-lectin.

In another aspect, this invention is a method for the production of an implantation device such as a stent, the device comprising a body having a surface, by applying an intermediate layer to at least a portion of the surface; and treating at least a portion of the surface with a solution comprising a receptor or a derivative thereof such that the receptor or the derivative thereof is attached to at least a portion of the surface.

In yet another aspect, this invention is a kit comprising an implantation device, such as a stent, comprising a body having a surface, wherein at least a portion of the surface is coated with a receptor capable of binding with a ligand formed by combining an active principle with a substance capable of binding to the receptor; and a preparation containing the ligand, which is capable of being put into contact with the device when desired.

In a preferred embodiment, the active principle is an antithrombogenic agent, an endothelialisation promoter, a radioactive isotope, a platelet antiaggregant agent, a fibrinolytic agent, an anti-inflammatory agent, an anti-proliferation agent, a radiopaque substance, a gene therapy agent, or an inhibitor and/or promoter of cellular adhesion and/or growth.

DETAILED DESCRIPTION OF THE PREFERRED EMBODIMENTS

According to the invention, the aforesaid active principle, which can have any desired function whatsoever, for example, therapeutic, diagnostic or to improve the biocompatability of the stent, is combined, without compromising its functionality and using known chemical reactions, with the substance capable of binding with the receptor to form the ligand.

This latter is then incorporated into a preparation suitable for administration, for example, transdermally or systemically, to a patient in which a stent coated with the receptor has been implanted. Following administration, bonds form between the receptor and the ligand which cause the active principle to attach to the surface of the stent which is then able to function.

This administration may occur at different times depending on the specific requirements of the case. The preparation containing the ligand may, in fact, be administered to the patient and thus come into contact with the stent either during implantation or at a subsequent time such as post-operatively or as an out-patient, as well during the handling of possible emergencies or complications.

The preparation containing the ligand may also be brought directly into contact with the stent before implantation such that the active principle is already attached to the surface of the stent to be implanted.

The present invention therefore confers a significant flexibility of application, both in terms of the timing of the administration of the preparations, and the variety of these latter which can be matched to a stent coated with a given receptor.

The receptor and the substance in the ligand capable of binding to the receptor can, for example, be chosen from the following pairs: streptavidin-biotin, biotin-streptavidin, avidin-biotin, biotin-avidin, antigen-antibody, antibody-antigen, lectin-glycoprotein and glycoprotein-lectin.

Streptavidin-biotin and avidin-biotin are the preferred pairings. These interactions are, in fact, the most intense biological interactions of the non-covalent type ($K_a=10^{15} M^{-1}$) known between a protein and a receptor, and the bond which forms is stable in a wide range of pH and temperature values and is resistant to organic solvents and other denaturing agents. In addition, the bond requires relatively mild conditions and short time periods for its formation. Further details of the avidin-biotin bond are given in "Avidin-Biotin Chemistry—A Handbook", AAVV, Pierce Publishing Company, 1992, the content of which is incorporated by reference in the present description.

The surface of the body of the implantation device can be coated directly or indirectly (for example, with an interposed intermediate layer), and completely or partly, using a polymeric material or metal, or a ceramic (for example, pyrolytic carbon).

A further subject of the present invention is a method for the production of an implantation device of the type described above, characterised in that it provides for the treatment of at least a portion of the surface of the body of the device with a solution containing a receptor or a derivative thereof such that the receptor or its derivative attaches to the portion.

Preferably, this method provides for the portion of the surface of the body of the device to be subjected to a preliminary treatment in order to bring it into contact with the solution, which treatment facilitates the attachment of the receptor or its derivative. Suitable preliminary treatments include bringing the surface into contact with an oxidising solution (e.g., an oxidant), a gas (e.g., ozone), and/or a plasma.

For example, this treatment can be an ammoniacal plasma treatment or a treatment with a substance capable of attaching to the surface and forming an anchorage site for the receptor or derivative thereof.

The term "active principle" comprises all of the substances capable of performing a medical function, for example, therapeutic or diagnostic, having either an immediate effect or one prolonged over time.

Generally, and provided, obviously, that no specific contra-indications related to their character exist, different active principles may be used, either alone or in a mixture in a single preparation. The composition of this latter will be reflected in the composition of the active principles attached to the stent surface.

Active principles appropriate to the invention could be, for example, antithrombogenic agents, endothelialisation promoters, radioactive isotopes, platelet antiaggregant agents, fibrinolytic agents, anti-inflammatory agents, antiproliferation agents, radiopaque substances, agents for gene therapy, inhibitors and/or promoters of cellular adhesion and/or growth.

Suitable active principles are generally those capable of improving the biocompatability and, in particular, the haemocompatability, of the implantation device, and of inhibiting the reactions which lead in the medium term to neointimal hyperplasia and the consequent reduction or occlusion of the vasal lumen.

The possibility offered by the invention of choosing the moment for administering the preparation containing the ligand to the patient is certainly advantageous where the active principle is an unstable or radioactive substance. As already indicated, in fact, such substances are preferably administered in specialist nuclear medicine units, which makes it impractical to administer them at the same time as implantation.

However, the invention enables the operations for implantation and the association therewith of a radioactive substance to be separated in time such that the implantation operation may be performed in units not provided with specific apparatus for nuclear medicine.

Even if, as indicated above, the ligand is brought into contact with the stent before it is implanted such that the device can be positioned with the active principle already bound to its surface, there are clear advantages of the invention. For example, the physician can decide, at the moment of implantation and depending on the characteristics of the patient and the specific procedure, which active principle or combination thereof, and in what doses, should be used in specific cases, choosing from a wide range of possible active principles available in a form associated with the ligand. Where radioisotopes having a biologically-active component are used, the invention has the significant advantage that the production, distribution and storage of the stent can be separated from those procedures relating to the radioisotopes; the former can thus be dealt with without the restrictions and complex security requirements relating to radioactive materials; conversely, a radioactive principle, for example, in the form of a solution or dispersion, can be produced separately by organisations specialising in radiopharmaceuticals and delivered to the user in limited quantities at the time of use, following procedures that are well known in the radiopharmaceuticals industry.

EXAMPLES

Further advantages and characteristics of the present invention will become clear from the following non-limiting examples.

Example 1

1A) Preparation of a Stent Coated with Streptavidin (Receptor)

I) A stent made from AISI 316 L steel is oxidised by immersion in a 2 g/l solution $KMnO_4$ in $H_2SO_4$ for 2 minutes.

II) After washing with distilled water, the stent is immersed for 30 minutes at ambient temperature in a solution of 2% polyethyleneimine (PEI, BASF) in water, then washed with distilled water and baked in an oven at 60° C. overnight, giving rise to —$NH_2$ groups on its surface.

III) The stent is then treated for one hour at ambient temperature and under agitation with a solution of $4*10^{-3}$ M biotin-N-hydroxysuccinimide-ester dissolved in dimethylformamide (dried on molecular sieves) and diluted in a ratio of 1:100 in 50 mM pH 8.5 borate buffer at the moment of use.

IV) After repeated washings of the stent with the pH 8.5 borate buffer, the biotinylated surface is treated for three hours at ambient temperature and under agitation with a solution of 1 microgram/ml streptavidin in 50 mM pH 7.4 phosphate buffer containing 0.1% BSA.

V) After washing with 50 mM pH 7.4 phosphate buffer, the streptavidin-coated surface of the stent is treated statically for one hour with a solution of 4% saccharose and 2% PVP in a 10 mM pH 7.4 phosphate buffer in order to form a protective covering over the streptavidin. The stent is then removed from the solution and, without washing, is dried at ambient temperature in a vacuum desiccator.

VI) The stent thus coated with streptavidin (the receptor) is stored in blisters and sterilised. The quantity of streptavidin bound to the surface, analysed using $^3$H-biotin, is 0.03 pmoles/cm$^2$.

1B) Obtaining Biotinylated Heparin (the Ligand)

I) 1 g heparin is dissolved in 300 ml distilled water at 0° C., 10 mg $NaNO_2$ are then added under agitation to the mixture formed in this way, and the pH taken to 2.7 by the addition of dilute HCl (1M).

II) The mixture is agitated for two hours at 0° C. and then the pH is adjusted to 7.0 using 1 M NaOH.

III) The mixture is dialysed with distilled water using three changes of water, each of 1 l.

IV) The dialysed mixture is concentrated to a small volume and lyophilized.

V) The lyophilized product thus obtained is treated with 0.1 M pH 5.5 acetate buffer to obtain a 0.5 mM solution in partially degraded heparin. An equivalent volume of a 5 mM solution biotin-LC-hydrazide (Pierce) dissolved in 0.1 M pH 5.5 acetate buffer is added. The reaction is allowed to continue for three hours at ambient temperature under agitation.

VI) The mixture thus obtained is dialysed with distilled water using three changes of water.

VII) The dialysed mixture is concentrated to a low volume and lyophilized, obtaining biotinylated heparin (ligand) which is dried at 4° C.

1C) Association of the Biotinylated Heparin with the Coated Stent

A preparation containing the ligand is formed at the moment of use by dissolving the biotinylated heparin (the ligand) in 50 mM pH 7.4 phosphate buffered saline (PBS).

This preparation can be brought into contact in vitro with the streptavidin-coated stent (the receptor) for 30 minutes in order to form the bonds between the receptor and the ligand before the surgical intervention to implant the stent. In this way, the heparin is associated beforehand with the surface of the stent which is then implanted.

Alternatively, the aforesaid preparation may be administered systemically to a patient in which the streptavidin-coated stent has already been implanted, thus similarly causing the formation in situ of the bonds between the receptor and the ligand and, as a consequence, the association of the heparin with the stent surface.

As a further alternative, the aforesaid preparation can be administered percutaneously to a patient at the same time as or after the intervention to implant the streptavidin-coated stent, thus causing the formation of the bonds between the receptor and the ligand and the association of the heparin with the stent surface in the same way.

Example 2

Example 2 is similar to example 1 with the exception of steps 1A-(I–II–III) which are replaced with the following:

I') A metal stent is coated with a layer of Parylene or polylactic acid and its copolymers with glycolic acid or e-caprolactone.

II') The coated stent is incubated at ambient temperature for 10 minutes in the dark with a solution containing 1 mg/ml photoactivatable biotin (Pierce), then irradiated for 15 minutes with electromagnetic radiation of a wavelength in the range 300–460 nm (preferably 350 nm).

III') The stent treated in this way is washed with a 50 mM pH 8.5 borate buffer.

Example 3

Example 3 is similar to example 1 with the exception of steps 1A-(I–II–III) which are replaced by the following:

I") A stent made from metal or a polymeric material is treated with plasma in ammonia, in order to introduce —$NH_2$ groups on to its surface.

Example 4

Example 4 is similar to example 1 with the exception of steps 1A-(I–II–III) which are replaced by the following:

I'") A stent made from metal or a polymeric material is treated with plasma in ammonia in order to introduce —$NH_2$ groups on to its surface.

II'") The stent treated in this way is brought into contact with streptavidin-N-hydroxysuccinimide-ester.

Examples 5–8 below refer to the preparation of different binding agents from those described in example 1B. These binding agents may be incorporated in preparations for use in association with a stent of the type described in any of the preceding examples 1A, 2, 3 and 4, in a manner similar to that indicated in paragraph 1C of example 1.

Example 5

I) 2 mg urokinase are dissolved in 100 ml 50 mM pH 8.5 bicarbonate buffer to form a first solution.

II) Immediately before use, a second solution is prepared of 30 mg sulfo-NHS-LC-biotin (Pierce) in 10 ml distilled water, and added to the first solution. The resulting mixture is incubated at 0° C. for two hours.

III) The unreacted and hydrolysed sulfo-NHS-LC-biotin is removed by gel filtration or dialysis.

IV) The resulting solution is concentrated to obtain biotinylated urokinase which is stored at −20° C.

Example 6

A preparation provided by Amersham on request is utilised as biotin 1,1-ddATPa[$^{32}$P].

Example 7

A preparation provided on request by the European Institute of Oncology—Milan/Amersham—Saluggia VC is used as D-$^{90}$Y-LC-DOTA-biotin.

Example 8

I) Sulfo-NHS-LC-biotin in 10 times excess is dissolved in distilled water is reacted with the -RGD peptide immobilised on a Merrifield resin containing a terminal —$NH_2$ group and having protected lateral groups.

II) After reaction with the sulfo-NHS-LC-biotin, the biotin -RGD peptide is released from the resin following a hydrolysis treatment.

III) The biotinylated -RGD peptide is desalted by gel filtration, lyophilized and stored at 4° C.

Example 9

A stent made from AISI 316 L steel and coated with Parylene is reacted in the dark for two hours with an aqueous solution, 10% DMF, 4 mM Sulfo-Sanpah (Pierce), a photoactivatable reagent. The stent is then exposed for several minutes to a light source which emits an appropriate wavelength (360 nm); this achieves the cross-linking of the photoreactive compound to the surface of the device. The washed and dried stent is then treated with a 50 mM solution dicyclohexylcarbodiimide(DCC) and 0.5 M N-hydroxysuccinimide in anhydrous DMF for 30 minutes; after washing with anhydrous DMF it is reacted with a 7 microgram/ml solution avidin in 50 mM pH 8.5 borate buffer for 30 minutes. After washing with a borate buffer, the stent is treated for one hour with a solution of 4% saccharose and 2% PVP in a 10 mM pH 7.4 phosphate buffer, in order to form a protective coating. Finally, the stent is removed from the solution and dried at ambient temperature under vacuum. In this case, the quantity of avidin bound to the surface, analysed using $^3$H-biotin, is 1.0 pmoles/cm$^2$.

Example 10

A coating of PEI is formed on the stent as described in steps I) and II) of example IA. It is then treated overnight and under agitation with a solution of 2% succinic anhydride in 1 M pH 6.0 phosphate buffer. The washed and dried stent is then treated with a solution of 50 mM DCC and 0.5 M N-hydroxysuccinimide in anhydrous DMF for 30 minutes; after washing with anhydrous DMF, it is treated with a solution of 7 microgram/ml avidin in 50 mM pH 8.5 borate buffer for 30 minutes. The stent, after washing with the borate buffer, is treated for one hour with a solution of 4% saccharose and 2% PVP in a 10 mM pH 7.4 phosphate buffer to form a protective coating. Finally, the stent is removed from the solution and dried under vacuum at ambient temperature.

Naturally, it is understood that while the principle of the invention remains the same, the details of manufacture and the embodiments may be widely varied with respect to that described, without this departing from the ambit of the present invention.

What is claimed is:

1. A method of administering an active principle at a desired location in the body of a patient comprising:
   providing an implantation device;
   coating the implantation device with a receptor;
   providing a preparation containing a ligand comprising an active principle combined with a substance capable of binding with the receptor;
   implanting the receptor coated implantation device at the desired location in the patient's body; and
   exposing the implantation device to the preparation containing the ligand in order to form a bond between the ligand and the receptor after the implantation device has been implanted in the patient's body.

2. The method of claim 1 wherein the provided implantation device has a body with a surface and wherein the method further comprises treating the surface of the body of the implantation device by bringing the surface into contact with at least one of an oxidizing solution, an oxidizing gas, and a plasma prior to coating the implantation device with the receptor.

3. The method of claim 2 wherein the step of treating the surface of the body of the implantation device comprises an ammoniacal plasma treatment.

4. The method of claim 1 wherein the provided implantation device has a body with a surface and wherein the method further comprises treating the surface of the body of the implantation device by bringing the surface into contact with a substance capable of attaching to the surface and forming an anchorage site for the receptor prior to coating the implantation device with the receptor.

5. The method of claim 1 wherein the step of exposing the implantation device to the preparation containing the ligand comprises administering the preparation percutaneously into the patient's body.

6. The method of claim 1 wherein the step of exposing the implantation device to the preparation containing the ligand comprises administering the preparation transdermally into the patient's body.

7. The method of claim 1 wherein the step of exposing the implantation device to the preparation containing the ligand comprises administering the preparation systemically into the patient's body.

8. The method of claim 1 wherein the step of providing the preparation containing the ligand comprises selecting the preparation such that the ligand comprises an active principle desirable for administration to the patient based upon the patent's needs.

9. A method of administering an active principle at a desired location in the body of a patient comprising:

providing an implantation device;

coating the implantation device with a receptor;

providing a preparation containing a ligand comprising an active principle combined with a substance capable of binding with the receptor;

placing the receptor coated implantation device in a package;

sterilizing the receptor coated implantation device;

removing the sterilized receptor coated implantation device from the package prior to implantation;

implanting the sterilized receptor coated implantation device at the desired location in the patient's body; and exposing the implantation device to the preparation containing the ligand after the sterilized receptor coated implantation device has been removed from the package in order to form a bond between the ligand and the receptor.

10. The method of claim 9 wherein the provided implantation device has a body with a surface and wherein the method further comprises treating the surface of the body of the implantation device by bringing the surface into contact with at least one of an oxidizing solution, an oxidizing gas, and a plasma prior to coating the implantation device with the receptor.

11. The method of claim 9 wherein the step of treating the surface of the body of the implantation device comprises an ammoniacal plasma treatment.

12. The method of claim 9 wherein the provided implantation device has a body with a surface and wherein the method further comprises treating the surface of the body of the implantation device by bringing the surface into contact with a substance capable of attaching to the surface and forming an anchorage site for the receptor prior to coating the implantation device with the receptor.

13. The method of claim 9 wherein the step of exposing the implantation device to the preparation containing the ligand occurs before the step of implanting.

14. The method of claim 9 wherein the step of exposing the implantation device to the preparation containing the ligand occurs after the step of implanting.

15. The method of claim 13 wherein the step of exposing the implantation device to the preparation containing the ligand comprises administering the preparation percutaneously into the patient's body.

16. The method of claim 13 wherein the step of exposing the implantation device to the preparation containing the ligand comprises administering the preparation transdermally into the patient's body.

17. The method of claim 13 wherein the step of exposing the implantation device to the preparation containing the ligand comprises administering the preparation systemically into the patient's body.

18. The method of claim 9 wherein the step of providing the preparation containing the ligand comprises selecting the preparation such that the ligand comprises an active principle desirable for administration to the patient based upon the patent's needs.

* * * * *